United States Patent [19]

Honan

[11] 4,175,562

[45] Nov. 27, 1979

[54] INTRAOCULAR PRESSURE APPLICATOR

[76] Inventor: Paul R. Honan, P.O. Box 588, 1720 N. Lebanon St., Lebanon, Ind. 46052

[21] Appl. No.: 811,549

[22] Filed: Jun. 30, 1977

[51] Int. Cl.² .............................................. A61B 17/00
[52] U.S. Cl. .................. 128/303 R; 128/163; 128/327
[58] Field of Search ............ 128/2 S, 2.05 G, 2.05 C, 128/327, 76.5, 163, 303 R

[56] References Cited

U.S. PATENT DOCUMENTS

| | | | |
|---|---|---|---|
| 2,690,173 | 9/1954 | Seeger et al. | 128/76.5 X |
| 3,628,536 | 12/1971 | Glesne | 128/327 |
| 3,756,239 | 9/1973 | Smythe | 128/2.05 C X |
| 3,779,236 | 12/1973 | Stewart | 128/2.05 G |
| 3,952,735 | 4/1976 | Wirtshafter et al. | 128/163 |

FOREIGN PATENT DOCUMENTS 209622  3/1968  U.S.S.R. ................................ 128/163

Primary Examiner—Robert W. Michell
Assistant Examiner—Michael H. Thaler
Attorney, Agent, or Firm—Woodard, Weikart, Emhardt & Naughton

[57] ABSTRACT

Disclosed is a cup-shaped bellows member removably attached to an adjustable headband. One end of the member is positioned to bear against the closed eyelid of a patient being prepared for intraocular surgery and upon whose head the headband has been placed. The opposite end of the bellows member is closed by a plate having a tubular portion communicating with the interior of the bellows portion and adapted to be connected to a means for increasing the pressure in monitored increments inside the chamber formed by the bellows and plate.

1 Claim, 4 Drawing Figures

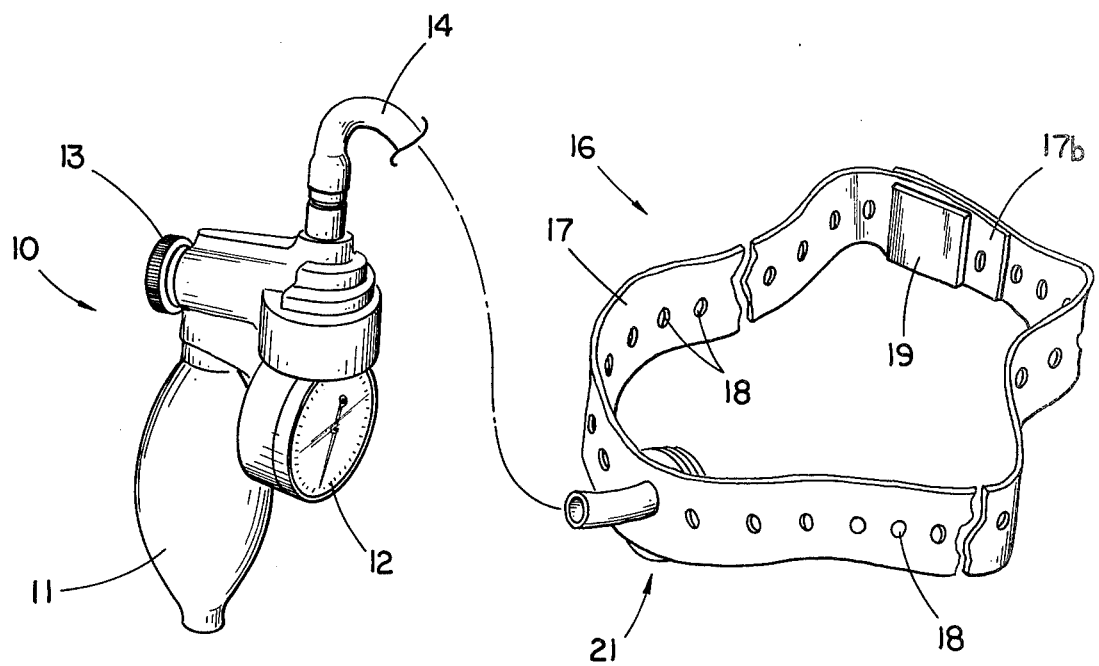
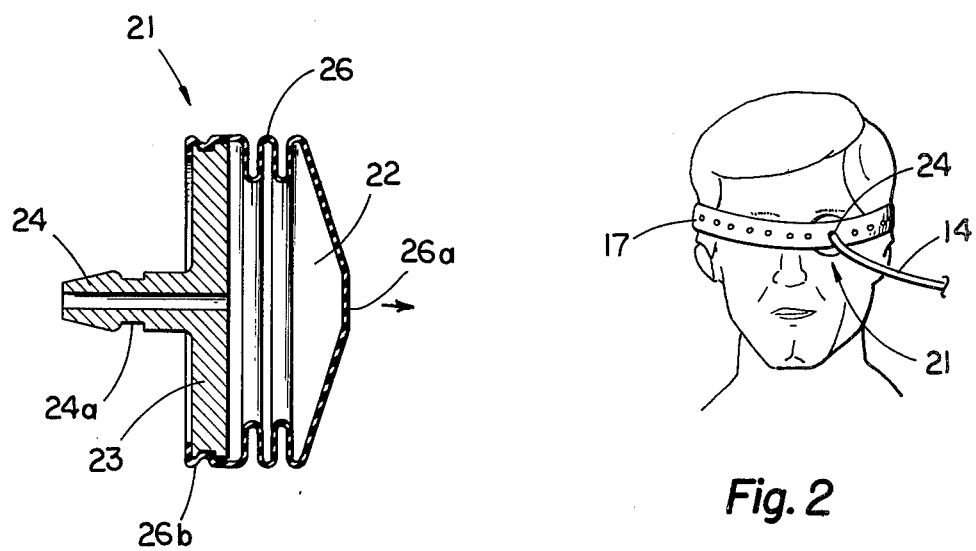
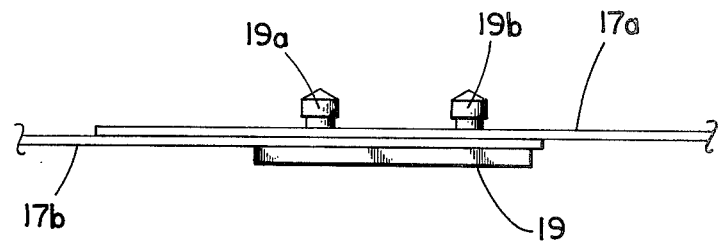

INTRAOCULAR PRESSURE APPLICATOR

BACKGROUND OF THE INVENTION

For many years surgeons have used digital pressure on the eye of a patient being prepared for intraocular surgery such as, for example, cataract surgery and implantation of intraocular lenses. The digital pressure is applied by the surgeon in magnitude and in duration in accord with his experience in creating the "soft eyes" condition helpful as a preconditioning of an eye to be subjected to intraocular surgery. This preconditioning of the eye lowers the intraocular pressure for the surgery and seems to aid in avoiding surgery induced vitreous humor loss. it has been theorized that pressure on the eye prior to intraocular surgery decreases the vitreous humor volume and may compress the retrobulbar fat pad. The result is a lessening of the tendency for the intraocular contents to bulge and escape from the eye during the surgery.

When the pressure to the eye is applied digitally by the surgeon, however, difficulties may arise. The magnitude of the pressure applied digitally varies from surgeon to surgeon, no precise measurement being available. Too much or too long applied pressure can cause dislocated lens within the eye. Because of possible occlusion of the central retinal artery by digital pressure, the pressure must be relieved at intervals during its application.

The apparatus of the present invention assures that a precisely predetermined pressure, visually monitored, is applied to the eye being prepared for surgery.

BRIEF DESCRIPTION OF THE DRAWINGS

FIG. 1 is a perspective view of apparatus embodying the present invention.

FIG. 2 is a perspective view of the apparatus in place on the head of a patient.

FIG. 3 is a side sectional view of the elastomeric bellows component of the apparatus.

FIG. 4 is a fragmentary top plan view of the adjustable securing means for the headband component of the apparatus.

DESCRIPTION OF THE PREFERRED EMBODIMENT

The device embodying the present invention includes a conventional sphygmomanometer hand aneroid gage and bulb indicated at 10. This component is well known in the art, used in manometric determining of blood pressure, and as here shown includes a rubber hand bulb 11, a pressure gage 12 and a relief valve manual operator 13. By successively squeezing the bulb 11 the pneumatic pressure is raised in the system. Check valving retains the pressure in the system until released by the manual operator 13. The gage 12 permits visual monitoring of the system pressure. A type of commercially available sphygmomanometer, suitable for this purpose, is Model HRI 8104-5098-03 manufactured by Taylor Instrument Consumer Products Division, Sybron Corporation, of Arden, N.C.

A flexible rubber tube 14 extends from the gage and bulb assembly 10 to a headband assembly 16. This assembly includes a headband proper, identified at 17, formed of elastomeric material, and provided with a series of longitudinally aligned apertures 18. As will be evident from FIGS. 2 and 4, the headband is adapted to encircle the head of the patient. Its length is adjustable by means of the fastening plate 19 (FIG. 4). Headed studs 19a and 19b, extending from one face of plate 18, are pushed through registering apertures 18 to hold the overlapping portions 17a and 17b of the headband in place on the head of the patient. It will be understood that the flat face of the plate 19 opposite the studs rests against the head of the patient.

The tube 14 extends to the member 21 which directly exerts pressure on the eye of the patient. Member 21 includes a chamber 22 (FIG. 3) having a rigid rear wall 23. A tubular element 24, which may be integral with the rear wall, accomodates the tube 14 and provides communication to the interior of the chamber. The chamber is bounded by a circular cup-shaped, bellows configurated, flexible portion 26, formed of rubber or other suitable elastomeric material, the closed end 26a providing a circular movable wall for a chamber 22 and tending to move, upon an increase in pressure in the chamber, in the direction of the arrow in FIG. 3. The marginal area 26b of the bellows grips the grooved periphery of the rear wall 23 and is sealed thereto.

The tubular portion 24, as will be evident from FIG. 3, has its tip adapted to receive the air supply tube 14 and has an inset collar 24a. The band apertures 18 are sized so as to closely accommodate the collar 24a when the tubular element 24 is pushed through the appropriate headband aperture. This provides an attachment of the member 21 to the headband 17 which permits limited pivotal movement of the member with respect to the band. The tube 14 is, of course, pushed over the element 24 after the tubular element is attached to the band 17.

In operation, as shown in FIG. 2, the headband, with member 21 attached, is installed on the head of the patient. The member 21 is positioned so that movable wall 26a of chamber 22 rests lightly against the closed eyelid of that eye of the patient being prepared for surgery. The tube 14 is attached to element 24 and hand bulb 11 is then pumped until the gage registers the desired pressure. This will be the pressure in chamber 22 and a measure of the force being exerted by wall 26a on the eye of the patient.

This precisely metered pressure may remain against the eye of the patient for the time period desired, release of the pressure being accomplished by turning the pressure relief knob 13.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A device for lowering intraocular pressure in preparation for intraocular surgery comprising a headband adapted to extend around the head of the surgery patient, a single, circular, cup-shaped member attached to said headband and forming a chamber having a movable wall at one end, said chamber forming member having a bellows configuration with said movable wall of the chamber being integral with its pleated sidewall and formed of elastomeric material, the end of said member opposite said moveable wall being rigid and attached to said headband, means for the attachment of said member to the headband permitting limited pivotal movement of the member with respect to the headband, said member being adapted to be positioned at the orbital cavity of and in overlying relation to that eye of the patient to be subjected to surgery with said movable wall contiguous with the closed eyelid of said eye, and means for increasing the pressure in said chamber in monitored increments to thereby apply through said movable wall a predetermined amount of pressure on said eye.

* * * * *